(12) United States Patent
Naito et al.

(10) Patent No.: US 11,609,201 B2
(45) Date of Patent: Mar. 21, 2023

(54) METHOD FOR MEASURING COMBUSTIBLE GAS CONCENTRATION, COMBUSTIBLE GAS SENSOR, AND COMBUSTIBLE GAS SENSOR PRODUCTION PROCESS

(71) Applicant: KABUSHIKI KAISHA TOSHIBA, Minato-ku (JP)

(72) Inventors: Katsuyuki Naito, Bunkyo (JP); Naomi Shida, Minato (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 711 days.

(21) Appl. No.: 16/563,575

(22) Filed: Sep. 6, 2019

(65) Prior Publication Data

US 2020/0284744 A1    Sep. 10, 2020

(30) Foreign Application Priority Data

Mar. 5, 2019 (JP) .............................. JP2019-039678

(51) Int. Cl.
*G01N 27/12* (2006.01)
*G01N 33/00* (2006.01)
*G01N 27/02* (2006.01)

(52) U.S. Cl.
CPC .......... *G01N 27/127* (2013.01); *G01N 27/021* (2013.01); *G01N 33/0047* (2013.01); *G01N 33/0057* (2013.01)

(58) Field of Classification Search
CPC .............. G01N 27/127; G01N 27/021; G01N 33/0047; G01N 33/0057

(Continued)

(56) References Cited

U.S. PATENT DOCUMENTS

| 4,579,751 A | 4/1986 | Forster |
| 10,379,095 B2 * | 8/2019 | Sambandan ....... G01N 33/0047 |

(Continued)

FOREIGN PATENT DOCUMENTS

| JP | 60-71942 A | 4/1985 |
| JP | 2016-163858 A | 9/2016 |

(Continued)

OTHER PUBLICATIONS

Chao Zhang, et al., "Room temperature responses of visible-light illuminated $WO_3$ sensors to $NO_2$ in sub-ppm range", Sensorsand Actuators B: Chemical, 181, 2013, pp. 395-401.

(Continued)

*Primary Examiner* — Farhana A Hoque
(74) *Attorney, Agent, or Firm* — Oblon, McClelland, Maier & Neustadt, L.L.P.

(57) ABSTRACT

The embodiments provide a method making it possible to safely and inexpensively measure concentrations of combustible gases, such as methanol, at room temperature even in high concentration atmospheres, and also provide a sensor making it possible to carry out the above measurement method. The measurement method comprises:

arranging a film containing nanoparticles of tungsten oxide and a pair of electrodes which are separated from each other and which individually keep in contact with said film in said atmosphere, exposing said film to light, measuring electric resistance change of said film before and after exposing said film to light, and determining said concentration based on said change.

19 Claims, 3 Drawing Sheets

(58) Field of Classification Search
USPC .......................................................... 324/693
See application file for complete search history.

(56) References Cited

U.S. PATENT DOCUMENTS

| | | | |
|---|---|---|---|
| 2006/0000259 A1 | 1/2006 | Rothschild et al. | |
| 2016/0169824 A1* | 6/2016 | Shin | G01N 27/12 73/31.06 |
| 2017/0307688 A1* | 10/2017 | Trainer | H02M 7/4835 |
| 2018/0210008 A1* | 7/2018 | Kuiper | G01Q 20/00 |

FOREIGN PATENT DOCUMENTS

| | | |
|---|---|---|
| JP | 2017-129570 A | 7/2017 |
| JP | 2017-519978 A | 7/2017 |
| JP | 2017-181996 A | 10/2017 |

OTHER PUBLICATIONS

Oriol Gonzalez, et al., "Using the Transient Response of $WO_3$ Nanoneedles under Pulsed UV Light in the Detection of $NH_3$ and $N_2$", Sensors, 18,1346, 2018, 13 pages.

* cited by examiner

FIG. 4

METHOD FOR MEASURING COMBUSTIBLE GAS CONCENTRATION, COMBUSTIBLE GAS SENSOR, AND COMBUSTIBLE GAS SENSOR PRODUCTION PROCESS

CROSS-REFERENCE TO RELATED APPLICATIONS

This application is based upon and claims the benefit of priority from the prior Japanese Patent Application No. 2019-039678, filed on Mar. 5, 2019, the entire contents of which are incorporated herein by reference.

FIELD

Embodiments of the present disclosure relate to a method for measuring combustible gas concentration, a combustible gas sensor, and a combustible gas sensor production process.

BACKGROUND

It is important for health and safety to measure concentrations of combustible gases and organic gases. Accordingly, there are various types of sensors for measuring gas concentrations. According to the kind and concentration of the gas intended to be measured, a suitable sensor is selected from them. For example, when the gas is thickly contained in the measurement atmosphere, particularly when the gas concentration is within or close to the explosion limit, it is seriously important to measure the gas concentration from the viewpoint of ensuring safety. In the measurement of such a high gas concentration, it is desired that the sensor itself does not work as an ignition source. In view of that, thermal conductivity sensors or infrared absorption sensors are often adopted. However, thermal conductivity sensors have low sensitivities to methanol, carbon monoxide, ammonia and the like, which have thermal conductivities near to that of the air. In addition, infrared absorption sensors are expensive because they need special optical parts.

Meanwhile, the above gases such as methanol, carbon monoxide and ammonia are important gaseous substances for power-to-chemical (P2C) technologies, with which they are produced by use of electric power or sunlight as energy sources. The gases are produced in high concentrations, and hence there is a high demand for gas sensors measuring concentrations thereof.

DETAILED DESCRIPTION

Embodiments will now be explained with reference to the accompanying drawings. Here, it should be noted that, in some embodiments, the same numbers are assigned to the common components and duplicate explanations thereof are omitted. Further, the drawings are schematic views illustrating the embodiments for the purpose of promoting understanding thereof, and hence, for example, shapes, dimensions, ratios and the like of the components are not necessarily the same as real ones and they can be desirably changed in designs by reference to the following explanations and known technologies.

A combustible gas concentration measurement method according to the embodiment is a method for measuring combustible gas concentration in a combustible gas atmosphere comprising:

arranging a film containing nanoparticles of tungsten oxide and a pair of electrodes which are separated from each other and which individually keep in contact with said film in said atmosphere, exposing said film to light, measuring electric resistance change of said film before and after exposing said film to light, and determining said concentration based on said change.

Also, a combustible gas sensor according to the embodiment comprises a non-electroconductive substrate, a tungsten oxide nanoparticle-containing film formed on said substrate, a pair of electrodes which are separated from each other and which individually keep in contact with said film, a resistance measuring instrument with which electric resistance is measured between said pair of electrodes, and a light source emitting visible light to which said film is exposed.

Further, a combustible gas sensor production process according to the embodiment comprises the steps of:

preparing a non-electroconductive substrate, forming a pair of electrodes which are separated from each other on said substrate, coating said substrate with a dispersion of tungsten oxide nanoparticles to form a dispersion layer which contact with said pair of electrodes, drying said dispersion layer to form a tungsten oxide nanoparticle-containing film, installing a light source at such a position that said film can be exposed to light, and installing a resistance measuring instrument with which electric resistance is measured between said pair of electrodes.

First Embodiment

Figure 1:
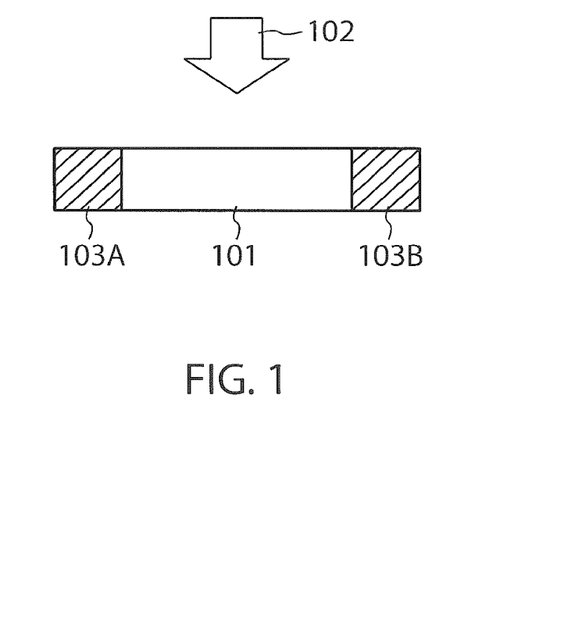
FIG. 1 is a schematic sectional view illustrating a combustible gas concentration measurement method according to the embodiment.

FIG. 1 shows a combustible gas concentration measurement method according to the embodiment, in which, for example, a tungsten oxide nanoparticle-containing film 101 (hereinafter, often simply referred to as "film") is exposed to visible light 102 and the electric resistance change at that time is measured between a pair of electrodes 103A and 103B.

The tungsten oxide nanoparticle is a n-type semiconductor and has a property of absorbing light of 500 nm or less wavelength. When the tungsten oxide nanoparticle absorbs the light, a thick depletion layer is formed on the surface thereof. Accordingly, the tungsten oxide nanoparticle-containing film generally has a high electric resistance. However, when the film is exposed to visible light in a combustible gas atmosphere, the combustible gas is oxidized to supply electrons into the tungsten oxide and consequently the depletion layer on the surface is thinned to reduce the electric resistance of the film. The measurement method of the embodiment utilizes this mechanism.

Normal gas-sensors with use of n-type semiconductors are generally heated with a heater to a high temperature before employed for measurements. However, in a thick gas atmosphere, there is a danger that the heater may work as an ignition source. Further, they are so sensitive that the response thereof tends to be saturated in high gas concentrations. Furthermore, if repeatedly used in high concentration atmospheres, they tend to deteriorate in reversibility and accordingly in measurement accuracy. In contrast, since it is unnecessary to heat the sensor, the method of the embodiment has high level of safety. It is also characteristic of the method according the embodiment to be hardly affected by moisture.

The method of the embodiment makes it possible to measure concentrations of highly reductive combustible gases, such as, methanol, carbon monoxide, ammonia and 2-propanol, even in high concentration atmospheres. Among the above gases, methanol has almost the same thermal conductivity as the air, and therefore relatively safe thermal conductivity sensors cannot be adopted for measuring concentration thereof. However, according to the embodiment, it can be safely measured even in an atmosphere containing methanol in a high concentration.

In the method of the embodiment, the film 101 is irradiated with light, to which the tungsten oxide nanoparticle preferably has a high absorbance. Specifically, the light preferably has a visible wavelength of 400 to 500 nm. As long as containing a light component having a wavelength of 400 to 500 nm, the applied light can be any color, such as, white, blue, violet or the like. Further, even UV light can be employed as long as containing a light component of 400 to 500 nm.

In the embodiment, the film contains tungsten oxide nanoparticles having a mean particle size of preferably 10 to 100 nm, more preferably 20 to 80 nm. If the mean particle size is excessively small, the nanoparticles tend to fuse together and consequently the film may flatten to reduce the area in contact with the combustible gas. On the other hand, if it is excessively large, the area where the nanoparticles keep in contact with each other is reduced and accordingly the resistance tends to change only a little when they are brought into contact with the combustible gas.

Even if the film consists of only tungsten oxide nanoparticles, it is possible to sensitively measure the concentration of highly reductive gas, such as, an alcohol (e.g., methanol, ethanol, or propanol) or an aldehyde (e.g., acetaldehyde or formaldehyde) according to the method of the embodiment.

However, in addition to the tungsten oxide nanoparticles, the film can further contain p-type semiconductor metal oxide nanoparticles, noble metal nanoparticles, or mixtures thereof. The p-type semiconductor metal oxide is preferably an oxide of nickel, copper, iron or molybdenum, and it may be a complex oxide thereof. The nanoparticles thereof have a mean particle size of preferably 10 to 200 nm, more preferably 30 to 150 nm. The film contains them preferably in an amount of 0.1 to 10 mass % based on the mass of the tungsten oxide. Meanwhile, the noble metal nanoparticles are nanoparticles of platinum, palladium, ruthenium or rhodium. They have a mean particle size of preferably 1 to 20 nm, more preferably 2 to 10 nm. The film contains them in an amount of preferably 0.001 to 1 mass %, more preferably 0.01 to 0.2 mass % based on the mass of the tungsten oxide. If the tungsten oxide-containing film further contains p-type semiconductor metal oxide nanoparticles, the sensitivity to toluene or acetone is enhanced. Specifically, when used in the measurement, the film exhibits characteristic behavior in that the resistance increases when exposed to light. If the tungsten oxide-containing film further contains noble metal nanoparticles, the sensitivity to methanol is so enhanced that the resistance decreases even in a low concentration methanol atmosphere. Further, the sensitivity to toluene, acetone or cyclohexane is also enhanced. Specifically, in that case, the film exhibits characteristic behavior in that the resistance increases when exposed to light.

In the embodiment, the mean diameter of particles is an average of diameters of circles that have the same areas as the projection areas obtained by electron microscopic observation of the particle surfaces.

The measurement sensitivity in the embodiment is enhanced if the tungsten oxide nanoparticle-containing film has crystallinity satisfying a particular condition. Specifically, in an X-ray diffraction (XRD) spectrum of the film, the ratio of the minimum intensity ($I_{min}$) to the maximum intensity ($I_{max}$) is preferably 0.5 to 0.8 in the 2Θ range of 22 to 26°. Here, the maximum intensity ($I_{max}$) and the minimum intensity ($I_{min}$) are obtained from the XRD spectrum of the film after noises are subtracted in the 2Θ range of 22 to 26°. If the intensity ratio is excessively small, the crystallinity is so high that the response to combustible gases tends to be saturated in high gas concentrations. On the other hand, if the ratio is excessively large, the film has such low crystallinity that the sensitivity to combustible gases tends to be lowered in high gas concentrations.

The measurement of XRD spectrum can be carried out, for example, under the following conditions:
XRD apparatus: SmartLab ([trademark], manufactured by Rigaku Corporation),
X-ray source/output: CuKα line/45 kV 200 mA,
optical system: focusing optics,
slit system:
  incident Soller 5.0°, ⅓° (w)×10 mm (h)
  light reception 20 mm (w)×20 mm (h), Soller 5.0°, 20 mm (w)×20 mm (h),
detector, attenuator: D/tex Ultra 259 (one-dimensional semiconductor detector),
auto scanning system: 2Θ/ω continuous scanning,
measuring range/measuring step/scanning speed: 15° to 90°/0.01°/10.0° per minute.

When the combustible gas changes in concentration under the measurement atmosphere, the electric resistance changes. Accordingly, the concentration change of the gas can be detected in the embodiment. Further, for the purpose of obtaining a calibration curve, the gas concentration may be intentionally changed to measure the electric resistances in various concentrations. By reference to the calibration curve, the absolute value of gas concentration can be estimated from the electric resistance.

Second Embodiment

Figure 2:
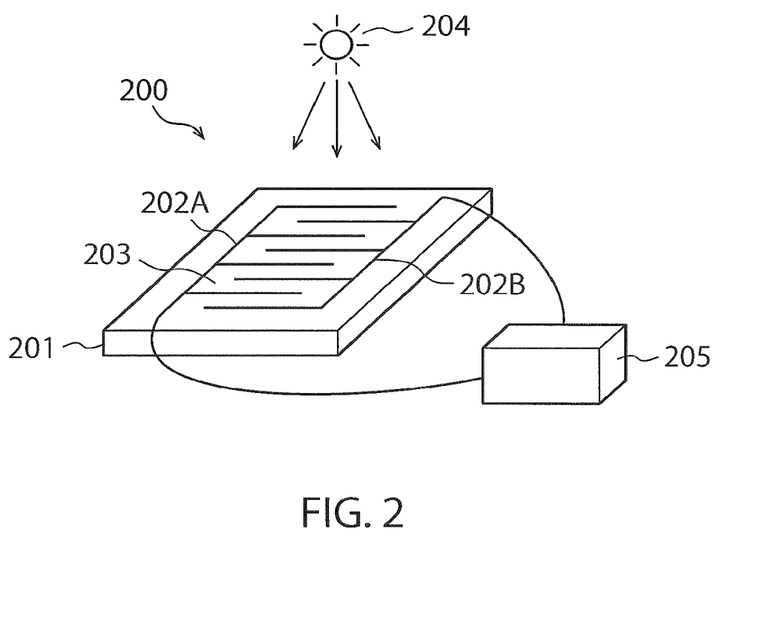
FIG. 2 is a conceptual sketch showing a structure example of a gas sensor according to the embodiment.

FIG. 2 is a conceptual sketch showing a structure example of a gas sensor according to the embodiment.

The gas sensor comprises a substrate 201, electrodes 202A and 202B for measuring the electric resistance, a tungsten oxide nanoparticle-containing film 203 in contact with the electrodes, a light source 204 from which visible light is applied to the tungsten oxide film, and a resistance measuring instrument 205 with which the electric resistance is measured between the electrodes 202A and 202B.

The substrate 201 is non-electroconductive. Specifically, it can be made of ceramics, paper or polymer. If the substrate is transparent, the later-described light source can be placed on the opposite side to the face on which the tungsten oxide nanoparticle-containing film is formed. The transparent substrate is, for example, made of glass or transparent polymer.

In the embodiment, the electrodes 202A and 202B can be in any shapes. Examples of the shapes include comb-like shapes, line shapes, and pad shapes. Among them, the electrodes in comb-like shapes are preferred from the viewpoint of downsizing the sensor. That is because it is possible to enlarge the contact area between the comb electrodes and the tungsten oxide film and accordingly it is easy to enhance the response even if the electrodes occupy only a small area.

The comb electrodes have a pitch of preferably 1 to 100 µm, more preferably 5 to 20 µm. The width thereof is preferably 5 to 100 µm, more preferably 5 to 20 µm. The number of pitches is preferably 100 to 1000. The length of the electrodes is preferably 5 to 20 mm. The comb electrodes are preferably made of gold or platinum because they have high corrosion resistance. The electrode substrate is preferably made of materials, such as glass and ceramics, from which the electrode material is hardly peeled off.

The electrodes in the embodiment may be positioned on, under or inside the tungsten oxide nanoparticle-containing film. However, in view of production easiness, it is preferred to form the electrodes on the substrate and then to form the film on the electrodes.

The tungsten oxide nanoparticle-containing film in the present embodiment may be the same as that explained in the first embodiment.

There are no particular restrictions on the thickness of the tungsten oxide nanoparticle-containing film. However, if the film is excessively thin, the electric resistance often changes too little to measure. On the other hand, if the film is excessively thick, the site at which the reaction is induced by light exposure is often so far apart from the electrodes as to lower the sensitivity. In consideration of those, the film has a thickness of preferably 0.5 to 5 µm, more preferably 1 to 3 µm.

The size and shape of the film can be desirably selected, but the film generally has a circular or rectangular shape. The diameter or the height and width thereof are generally 5 to 30 mm.

The light source 204 in the present embodiment may be any desired light source as long as it can emit visible light, particularly, light containing a light component having a wavelength of 400 to 500 nm. Examples thereof include while, blue and violet LEDs. The LED light source makes it possible to downsize the sensor and hence to save energy. In addition, because the sensor can be operated with a low voltage, it is easy to ensure safety even in a combustible gas atmosphere.

The light source needs to be so placed as not to seriously prevent the combustible gas from diffusing into the tungsten oxide film. On the other hand, the film is preferably exposed homogeneously to the emitted light. In view of those, the gap between the light source and the film is preferably 1/10 to 1/3 of maximum film width. The light source is preferably supported above the film with three to six supporting legs. Further, if transparent material is adopted for the substrate, the light source can be placed on the side opposite to the film. Still further, in a gas-permeable cylindrical case, the tungsten oxide nanoparticle-containing film and the light source can be placed on the inside bottom and on the inside top, respectively.

The tungsten oxide film in the present embodiment may contain a metal oxide other than the above. Specifically, if containing fibrous alumina hydrate, the film is improved in evenness and robustness.

The resistance measuring instrument 205 is desirably selected from generally used ohmmeters and the like according to the electric resistance intended to be measured.

Third Embodiment

FIG. 3 schematically illustrates the flow of a gas sensor production process according to the embodiment. The combustible gas sensor production process according to the embodiment comprises the steps of:
preparing a non-electroconductive substrate,
forming electrodes on said substrate,
coating said substrate with a dispersion of tungsten oxide nanoparticles to form a dispersion layer,
drying said dispersion layer to form a tungsten oxide nanoparticle-containing film, and
installing a light source at such a position that said film can be exposed to light.

Figure 3A:
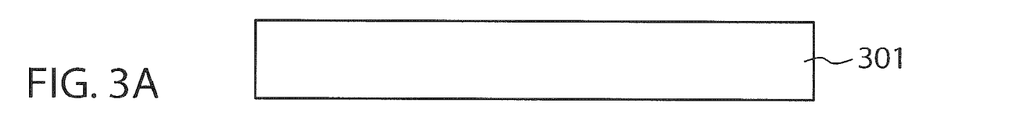
FIGS. 3A to 3E schematically illustrate the flow of a gas sensor production process according to the embodiment.

First, a non-electroconductive substrate 301 is prepared (FIG. 3(A)). The substrate must be non-electroconductive so as not to interfere when the electric resistance of the film is measured. Accordingly, it may be an electroconductive substrate covered with a non-electroconductive material.

Figure 3B:
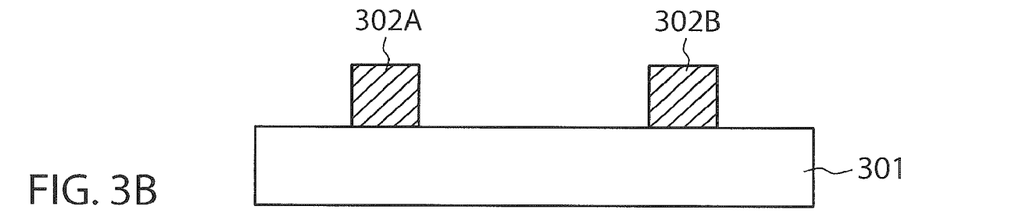

Then, electrodes 302 are formed on the surface of the non-electroconductive substrate 301 (FIG. 3(B)). The electrodes can be formed in a desired manner, which is specifically selected from sputtering, coating, printing, transferring or the like. As described above, the electrodes can be in any shapes. However, they preferably have comb-like shapes. That is because the substrate surface is so roughened that the dispersion layer successively formed thereon can be readily spread evenly.

Figure 3C:
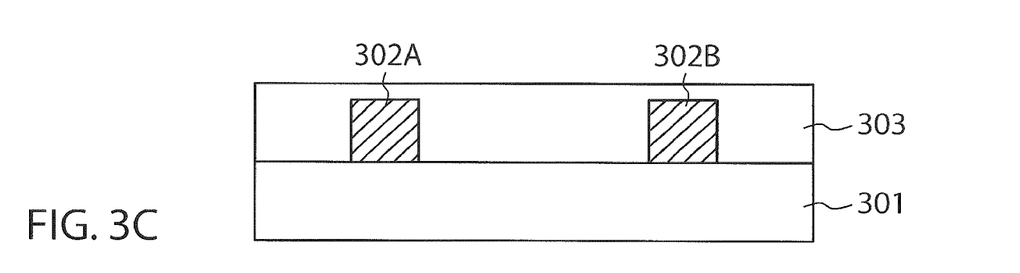

Subsequently, the substrate provided with the electrodes thereon is coated with a dispersion of tungsten oxide nanoparticles, to form a dispersion layer 303 (FIG. 3(C)). The dispersion contains the aforementioned tungsten oxide nanoparticles. In view of the production process, the tungsten oxide nanoparticles preferably have a mean particle size of 10 to 100 nm. If the mean particle size is larger than 100 nm, the dispersion tends to have poor homogeneity. On the other hand, if it is smaller than 10 nm, the film obtained by drying tends to have small surface area.

As a medium of the dispersion, any desired liquid can be employed as long as it does not give adverse effects to the ingredients or the substrate. Specifically, the dispersion medium is preferably water or aqueous solutions of alcohols. From the viewpoints of treatability and safety, water is preferred. However, aqueous solutions of alcohols have some merits. They can stably disperse the tungsten oxide nanoparticles and nanoparticles of other metal oxides or metals, which are optionally added according to necessity. In addition, they have enough low surface tensions to evenly spread on the substrate. Preferred examples of the alcohols include ethanol, methanol and isopropanol.

The content of the tungsten oxide nanoparticles in the dispersion can be desirably selected according to the coating method and the like, but is generally 1 to 10 mass % based on the total mass of the dispersion.

In the present embodiment, the dispersion may contain p-type semiconductor metal oxide nanoparticles, noble metal nanoparticles, or mixtures thereof.

The p-type semiconductor metal oxide nanoparticles can be desirably selected from those described above. In the production process, they tend to be positively charged while tungsten oxide tends to be negatively charged, and accordingly the p-type semiconductor metal oxide nanoparticles tend to be combined with tungsten oxide and consequently the durability of the film tends to be enhanced after drying. The noble metal nanoparticles can be also desirably selected from those described above. In the production process, they tend to be negatively charged and are small enough to disperse homogeneously in the tungsten oxide film. Because of that, they make it easy to obtain the effect of the embodiment even in a small amount.

In addition, the dispersion can furthermore contain other metal oxides. Specifically, if the dispersion contains fibrous alumina hydrate in particular, the photocatalyst particles are prevented from aggregation and accordingly it becomes possible to form a homogeneous and durable photocatalyst layer.

The dispersion can further contain a compound having a Si—O bond. Examples of the compound include silica and siloxane. The compound can improve wear resistance of the film and also can prevent deterioration of the substrate caused by the catalytic action of the tungsten oxide.

The dispersion can furthermore contain graphene oxide or graphite oxide. They prevent the tungsten oxide nanoparticles from aggregation in the dispersion, so as to keep the stability and activity of the dispersion for a long time.

The dispersion employed in the present embodiment can be applied by drop-coating, spin-coating, inkjet coating or the like. According to those coating methods, even a small amount of the dispersion can be lied on the substrate.

Figure 3D:
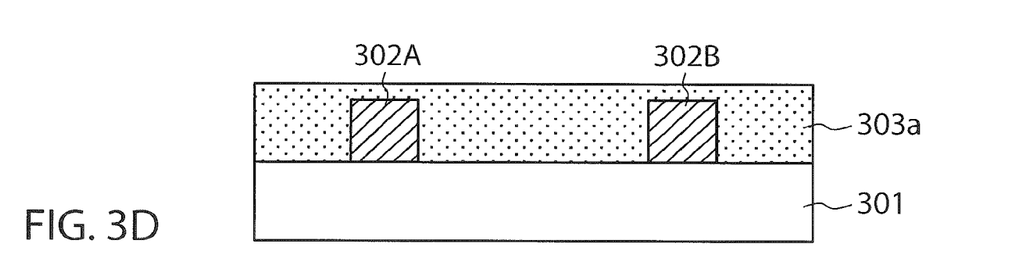
Figure 3E:
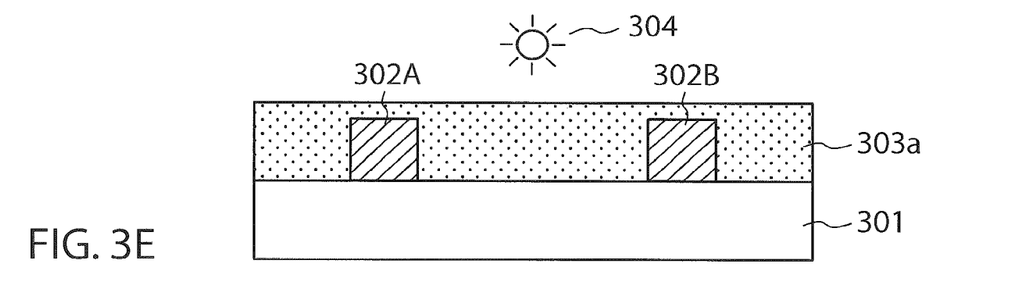

Successively, the formed dispersion layer is dried to produce a tungsten oxide nanoparticle-containing film 303a (FIG. 3(D)). In the drying procedure, the dispersion layer is heated at a temperature of preferably 5 to 100° C., more preferably 15 to 60° C. The temperature is set to be 100° C. or less in order to prevent the tungsten oxide nanoparticles from aggregation, so that the electric resistance may not become too low. On the other hand, the temperature is set to be 5° C. or more so that the dispersion layer can be naturally dried. Specifically, the layer is preferably dried by hot blowing or IR irradiation, and the hot blowing is particularly preferred because the temperature can be easily controlled.

After the drying procedure, additional heating treatment can be carried out at a higher temperature, if necessary. The treatment can enlarge the mean size of the particles and thereby can control the contact areas and/or voids among the particles. Accordingly, the sensitivity of the sensor can be controlled by the treatment.

After the film is dried, a light source 304 is installed (FIG. 3 (E)). The light source can be set in any desired form. For example, three to six supporting legs (not shown) are stood and the light source is supported with them. Further, if transparent material is adopted for the substrate, the light source can be placed on the side opposite to the tungsten oxide nanoparticle-containing film.

The gas sensor production process according to the embodiment is explained above with reference to FIG. 3. However, if necessary, the order of the steps can be changed. For example, either or both of the electrodes 302A and 302B can be formed after the tungsten oxide film 303a is formed. Further, if the substrate 301 is transparent, the light source 304 can be installed in any desired step.

EXAMPLES

The following examples will explain the embodiments more specifically.

Example 1

Platinum comb electrodes (10-μm width, 10-μm pitch; width: 5 mm; length: 5 mm) formed on a glass substrate are drop-coated with 20 μL of a 3 mass % aqueous dispersion of tungsten oxide nanoparticles having a mean particle size of 40 nm, and then dried by hot blowing at 60° C. for 30 minute to produce a tungsten oxide nanoparticle-containing film. While the film is exposed to white LED light of 15000 lux at room temperature in air, a direct current of 3 μA is applied between the electrodes and at the same time the voltage (about 1 V) is measured. Subsequently, when the film is exposed to 17 vol % methanol vapor, the voltage decreases rapidly and, after 3 minutes the resistance decreases by 70%. When the film is returned into the atmosphere, the resistance returns back to the initial value. The film exhibits good resistance to this repetition. The resistance decreases by 9% in 3.5 vol % methanol vapor and by 4% in 1.2 vol % methanol vapor.

Figure 4:
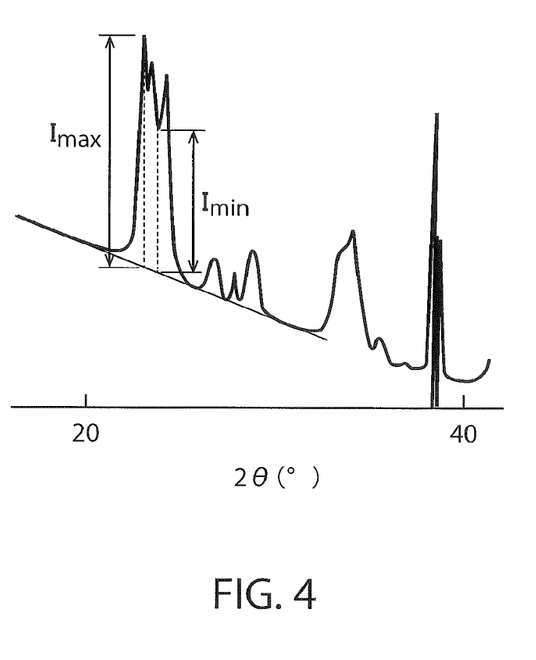
FIG. 4 is an X-ray diffraction spectrum of the tungsten oxide film in Example 1.

FIG. 4 shows an X-ray diffraction (XRD) spectrum of the tungsten oxide nanoparticle film. In the shown spectrum, the ratio of the minimum intensity to the maximum intensity is 0.64 in the 2Θ range of 22 to 26°.

Comparative Example 1

The procedure of Example 1 is repeated except that the film is not exposed to white LED light. When the film is exposed to 17 vol % methanol vapor, the resistance decreases by 6%.

Example 2

Platinum comb electrodes (10-μm width, 10-μm pitch; width: 5 mm; length: 5 mm) formed on a glass substrate are drop-coated with 20 μL of a 3 mass % aqueous dispersion of tungsten oxide nanoparticles having a mean particle size of 40 nm, and then dried by hot blowing at 60° C. for 30 minute to produce a tungsten oxide nanoparticle-containing film. The film is then heated at 600° C. for 1 hour, and thereby the mean particle size of the tungsten oxide nanoparticles is increased to 110 nm. While the film is exposed to white LED light of 15000 lux at room temperature in air, a direct current of 30 μA is applied between the electrodes and at the same time the voltage (about 1 V) is measured. Subsequently, when the film is exposed to 17 vol % methanol vapor, the voltage decreases rapidly and, after 3 minutes the resistance decreases by 20%. When the film is returned into the atmosphere, the resistance returns back to the initial value. The film exhibits good resistance to this repetition.

In an X-ray diffraction (XRD) spectrum of the tungsten oxide nanoparticle film, the ratio of the minimum intensity to the maximum intensity is found to be 0.29 in the 2Θ range of 22 to 26°. This indicate that the film has high crystallinity.

Example 3

Platinum nanoparticles having a mean particle size of 2 nm are added into a 3 mass % aqueous dispersion of tungsten oxide nanoparticles having a mean particle size of 40 nm. The amount of the platinum nanoparticles is 0.1 mass % based on the mass of the tungsten oxide. Thereafter, platinum comb electrodes (10-μm width, 10-μm pitch; width: 5 mm; length: 5 mm) formed on a glass substrate are drop-coated with 20 μL of the obtained dispersion, and then dried by hot blowing at 60° C. for 30 minute to produce a tungsten oxide nanoparticle-containing film. While the film is exposed to white LED light of 15000 lux at room temperature in air, a direct current of 3 μA is applied between the electrodes and at the same time the voltage (about 1 V) is measured. Subsequently, when the film is exposed to 120 ppm methanol vapor, the voltage decreases rapidly and, after 3 minutes the resistance decreases by 7%. When the film is exposed to 5 ppm methanol vapor, the resistance decreases by 2%. When the film is returned into the atmosphere, the resistance returns back to the initial value. The film exhibits good resistance to this repetition. When the film is exposed to 2 ppm or 3% toluene vapor, the resistance increases by 6% or 20%, respectively. When the film is returned into the atmosphere, the resistance returns back to the initial value. The film also exhibits good resistance to this repetition.

Example 4

Iron-nickel complex oxide nanoparticles having a mean particle size of 200 nm are added into a 3 mass % aqueous dispersion of tungsten oxide nanoparticles having a mean particle size of 40 nm. The amount of the complex oxide nanoparticles is 2 mass % based on the mass of the tungsten oxide. Thereafter, platinum comb electrodes (10-μm width, 10-μm pitch; width: 5 mm; length: 5 mm) formed on a glass substrate are drop-coated with 20 μL of the obtained dispersion, and then dried by hot blowing at 60° C. for 30 minute to produce a tungsten oxide nanoparticle-containing film. While the film is exposed to white LED light of 15000 lux at room temperature in air, a direct current of 3 μA is applied between the electrodes and at the same time the voltage (about 1 V) is measured. When the film is exposed to 3% toluene vapor, the resistance increases by 20%. When the film is returned into the atmosphere, the resistance returns back to the initial value. The film exhibits good resistance to this repetition.

Example 5

Iron-nickel complex oxide nanoparticles having a mean particle size of 200 nm and platinum nanoparticles having a mean particle size of 2 nm are added into a 3 mass % aqueous dispersion of tungsten oxide nanoparticles having a mean particle size of 40 nm. The amounts of the complex oxide nanoparticles and the platinum nanoparticles are 2 mass % and 0.01 mass %, respectively, based on the mass of the tungsten oxide. Thereafter, platinum comb electrodes (10-μm width, 10-μm pitch; width: 5 mm; length: 5 mm) formed on a glass substrate are drop-coated with 20 μL of the obtained dispersion, and then dried by hot blowing at 60° C. for 30 minute to produce a tungsten oxide nanoparticle-containing film. While the film is exposed to white LED light of 15000 lux at room temperature in air, a direct current of 3 μA is applied between the electrodes and at the same time the voltage (about 1 V) is measured. When the film is exposed to 3% toluene vapor, the resistance increases by 30%. When the film is returned into the atmosphere, the resistance returns back to the initial value. The film exhibits good resistance to this repetition.

Example 6

Platinum comb electrodes (10-μm width, 10-μm pitch; width: 5 mm; length: 5 mm) formed on a glass substrate are drop-coated with 20 μL of a 3 mass % aqueous dispersion of tungsten oxide nanoparticles having a mean particle size of 40 nm, and then dried by hot blowing at 60° C. for 30 minute to produce a tungsten oxide nanoparticle-containing film. The comb electrodes are then wired, and independently a white LED chip is fixed at three points above the substrate so that it may be separated from the tungsten oxide film by 1.5 mm. The wiring of the electrodes and that for driving the LED are together housed in a socket unified with the substrate, to produce a sensor head. While the head is connected with a DC power supply to drive the LED, a direct current of 3 μA is applied and at the same time the voltage (about 1 V) is measured. Subsequently, when the sensor head is exposed to 17 vol % methanol vapor, the voltage decreases rapidly and, after 3 minutes the resistance decreases by 60%. When the head is returned into the atmosphere, the resistance returns back to the initial value. The head exhibits good resistance to this repetition.

DESCRIPTION OF THE REFERENCE NUMERALS

101: tungsten oxide nanoparticle-containing film,
102: visible light,
103A, 103B: electrode,
200: gas sensor,
201: substrate,
202A, 202B: electrode,
203: tungsten oxide nanoparticle-containing film,
204: light source,
205: resistance measuring instrument,
301: substrate,
302A, 302B: electrode,
303: dispersion layer,
303a: tungsten oxide nanoparticle-containing film,
304: light source While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fail within the scope and sprit of the invention.

The invention claimed is:

1. A method for measuring combustible gas concentration in a combustible gas atmosphere, comprising:
arranging a film comprising nanoparticles of tungsten oxide and a pair of electrodes which are separated from each other;
while the film is exposed to light, measuring electric resistances of the film when the film is in contact with an atmosphere which does not contain the combustible gas and when the film is in contact with a combustible gas atmosphere; and
determining the combustible gas concentration based on a change between the electric resistances of the film.

2. The method according to claim 1, wherein the combustible gas is methanol.

3. The method according to claim 1, wherein the light has a wavelength of 400 to 500 nm.

4. The method according to claim 1, wherein the nanoparticles of tungsten oxide have a mean particle size of 10 to 100 nm.

5. The method according to claim 1, wherein the film further comprises p-type semiconductor metal oxide nanoparticles, noble metal nanoparticles, or mixtures thereof.

6. The method according to claim 1, wherein the film shows an X-ray diffraction spectrum in which the ratio of the minimum intensity to the maximum intensity is 0.5 to 0.8 in the 2Θ range of 22 to 26°.

7. A combustible gas sensor comprising;
a non-electroconductive substrate,
a tungsten oxide nanoparticle-containing film formed on the substrate,
a pair of electrodes which are separated from each other and which individually keep in contact with the film,
a resistance measuring instrument with which electric resistance is measured between the pair of electrodes, and
a light source emitting visible light to which the film is exposed.

8. The gas sensor according to claim 7, wherein the electrodes are comb electrodes formed between the substrate and the film.

9. The gas sensor according to claim 7, wherein the light source is a LED capable of emitting light having a wavelength of 400 to 500 nm.

10. The gas sensor according to claim 7, wherein the tungsten oxide nanoparticles have a mean particle size of 10 to 100 nm.

11. The gas sensor according to claim 7, wherein the film shows an X-ray diffraction spectrum in which the ratio of the minimum intensity to the maximum intensity is 0.5 to 0.8 in the 2Θ range of 22 to 26°.

12. The gas sensor according to claim 7, wherein the gap between the light source and the film is 1/10 to 1/3 of maximum width of the film.

13. The gas sensor according to claim 7, wherein the light source is supported above the substrate with three to six supporting legs.

14. A combustible gas sensor production process comprising:
preparing a non-electroconductive substrate,
forming a pair of electrodes which are separated from each other on the substrate,
coating the substrate with a dispersion of tungsten oxide nanoparticles to form a dispersion layer which contact with the pair of electrodes,
drying the dispersion layer to form a tungsten oxide nanoparticle-containing film,
installing a light source at such a position that the film can be exposed to light, and
installing a resistance measuring instrument with which electric resistance is measured between the pair of electrodes.

15. The process according to claim 14, wherein the electrodes have comb-like shapes.

16. The process according to claim 14. wherein the tungsten oxide nanoparticles have a mean particle size of 10 to 100 nm.

17. The process according to claim 14, wherein the dispersion further contains p-type semiconductor metal oxide nanoparticles, noble metal nanoparticles, or mixtures thereof.

18. The method according to claim 1, wherein the combustible gas is selected from the group consisting of methanol, carbon monoxide, ammonia and 2-propanol.

19. The method according to claim 1, wherein the concentration of the combustible gas is from 1.2 to 17% by volume.

\* \* \* \* \*